(12) United States Patent
Tomiyama et al.

(10) Patent No.: US 7,026,003 B2
(45) Date of Patent: Apr. 11, 2006

(54) PROCESSES FOR PREPARING AN ASPARTAME SLURRY

(75) Inventors: Yasuyuki Tomiyama, Kawasaki (JP); Masato Kawauchi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 309 days.

(21) Appl. No.: 10/300,797

(22) Filed: Nov. 21, 2002

(65) Prior Publication Data

US 2003/0096048 A1    May 22, 2003

(30) Foreign Application Priority Data

Nov. 22, 2001 (JP) .............................. 2001-358280

(51) Int. Cl.
*A23L 1/236* (2006.01)

(52) U.S. Cl. ...................... 426/548; 426/321; 426/335; 560/40

(58) Field of Classification Search ................ 426/321, 426/335, 548; 560/40
See application file for complete search history.

(56) References Cited

U.S. PATENT DOCUMENTS

| 5,502,238 | A |   | 3/1996 | Rijkers et al. |
|---|---|---|---|---|
| 5,536,510 | A | * | 7/1996 | Tyrpin et al. .................. 426/4 |
| 6,069,362 | A |   | 5/2000 | Giakos |
| 6,096,362 | A |   | 8/2000 | Hoek et al. |

FOREIGN PATENT DOCUMENTS

| EP | 0 978 518 | 2/2000 |
|---|---|---|
| WO | WO 99/64445 | 12/1999 |

* cited by examiner

*Primary Examiner*—Leslie Wong
(74) *Attorney, Agent, or Firm*—Oblon, Spivak, McClelland, Maier & Neustadt, P.C.

(57) ABSTRACT

The present invention provides processes for preparing a slurry containing aspartame, which is stable and is useful as a sweetener; as well as methods of assessing the stability of an aspartame slurry.

16 Claims, 2 Drawing Sheets

PROCESSES FOR PREPARING AN ASPARTAME SLURRY

BACKGROUND OF THE INVENTION

1. Field of the Invention

The present invention provides processes for preparing a slurry containing aspartame, which is stable and is useful as a sweetener; as well as methods of assessing the stability of an aspartame slurry.

2. Discussion of the Background

Slurries of aspartame (APM) are known and are used as a liquid sweetener. In addition, various methods of preparing such APM slurries have been described previously, for example, in Japanese Patent Kokai Publications JP-A-59-31669, 59-31656 and 59-151848; International Patent Publication WO 95/15697; and European Patent No. 102032. However, provided ways to maintain the physical stability of the slurry when stored have not been sufficiently addressed.

There have been several investigations concerning the physical preservation stability of APM slurry, for example, WO 95/15697 describes a method of making small APM particle sizes whereby the viscosity of the slurry increases and the stability is improved without precipitation of the particles. However, when the viscosity is particularly high the fluidity of the slurry makes it difficult to handle.

In Japanese Patent Kokai Publication JP-A-11-313636, methods of improving the physical stability upon storage were investigated and reported that if the particle size of APM is adjusted to not more than 10 μm or, preferably, not more than 8 μm in terms of the average diameter and when the slurry is prepared to have a relatively low viscosity, such as 100 mPa·s or lower, there was no precipitation of the resultant slurry. However, this method failed to provide a homogenous dispersion of the APM particles in the slurry, and often the dispersions prepared were found to be unstable.

In general, there are two methods for crystallizing APM. One method involves a stirring crystallization where the crystallization is effected by cooling a solution while it is being stirred. The second method involves static crystallization where the crystallization is effected by cooling without stirring the solution. These methods are described in Japanese Patent Kokai Publication JP-A-58-177952.

The APM crystals obtained by static crystallization have broader short axis diameter relative to the APM crystals obtained in by stirring crystallization. Therefore, the APM crystals obtained by the static crystallization exhibit excellent properties in terms of ease of handling in a solid-liquid separation and as a powder. As a result, static crystallization is commonly employed as the industrial crystallization process.

However, even when employing static crystallization as the production method, the resulting size of the APM particles is highly variable and can vary based on the impurities in the crystallization solution, such as salt. For example, while the differences are dependent on the conditions used for crystallization, the APM crystal particle size is about 6 μm in terms of a median diameter measured by a particle size distribution meter when APM hydrochloride is neutralized at a high temperature and then subjected to a static cooling, also known as a one-step crystallization. In a two-step crystallization whereby the crystals are separated, dissolved in water again, and then subjected to a static crystallization, the concentration of impurities is significantly lower, and the size of the resultant crystals is about 20 μm, which will vary depending on the actual conditions used for the crystallization.

When the large APM crystals are formulated in to a low viscosity slurry, the APM particles must be ground to adjust the particle size. In addition, when the APM crystals obtained from a stirring crystallization, which are much smaller and fine, are dried, blocks and big lumps typically form and, therefore, it is also necessary to grind the crystals when formulating the crystals into a slurry.

Since APM slurries are commonly used for foods, anti-microbiological preservation is critical. To impart that anti-microbiological preservation, sodium benzoate has been added; and the effective pH where sodium benzoate imparts the preserving effect is at a pH of 4 or lower (Japanese Patent Kokai Publication JP-A-11-313636).

While no precipitation of APM particles are observed in a slurry with APM particles of a specific median diameter such as 10 μm or less, which is at a pH of 4 or less, flocculation, which is coagulation due to aggregation of the particles is observed. As a result of this flocculation, the fluidity is compromised whereby the resultant APM slurry is not stable upon storage.

Therefore, there remains a need to solve this flocculation problem and provide a homogenously dispersed APM slurry that is stable and can be maintained at a pH suitable for anti-microbiological preservation upon storage.

SUMMARY OF THE INVENTION

Accordingly, the present invention provides methods of solving this problem and as a result, one object of the present invention is a process for preparing an aspartame slurry by adjusting the median diameter size of aspartame crystals to not more than 10 μm; mixing the aspartame crystals in a dispersing medium; and adjusting the pH of the resultant slurry to a pH suitable for maintaining antimicrobial conditions in the slurry, wherein after the mixing, the slurry exhibits a monomodal size distribution at not more than about 1000 μm.

Another object of the present invention is to provide a stable aspartame slurry with aspartame crystals which are of a median particle size of not more than 10 μm, which has a pH suitable for maintaining antimicrobial conditions in the slurry, and wherein the slurry exhibits a monomodal size distribution at not more than about 1000 μm.

Another object of the present invention is to provide a process for assessing the stability of an aspartame slurry, by measuring the median particle size distribution of the aspartame in the slurry, where the presence of a monomodal size distribution in a range of not more than 1000 μm is indicative that the aspartame slurry is stable, and where the presence of a multimodal size distribution is indicative that the aspartame slurry is not stable.

DETAILED DESCRIPTION OF THE INVENTION

Figure 1:
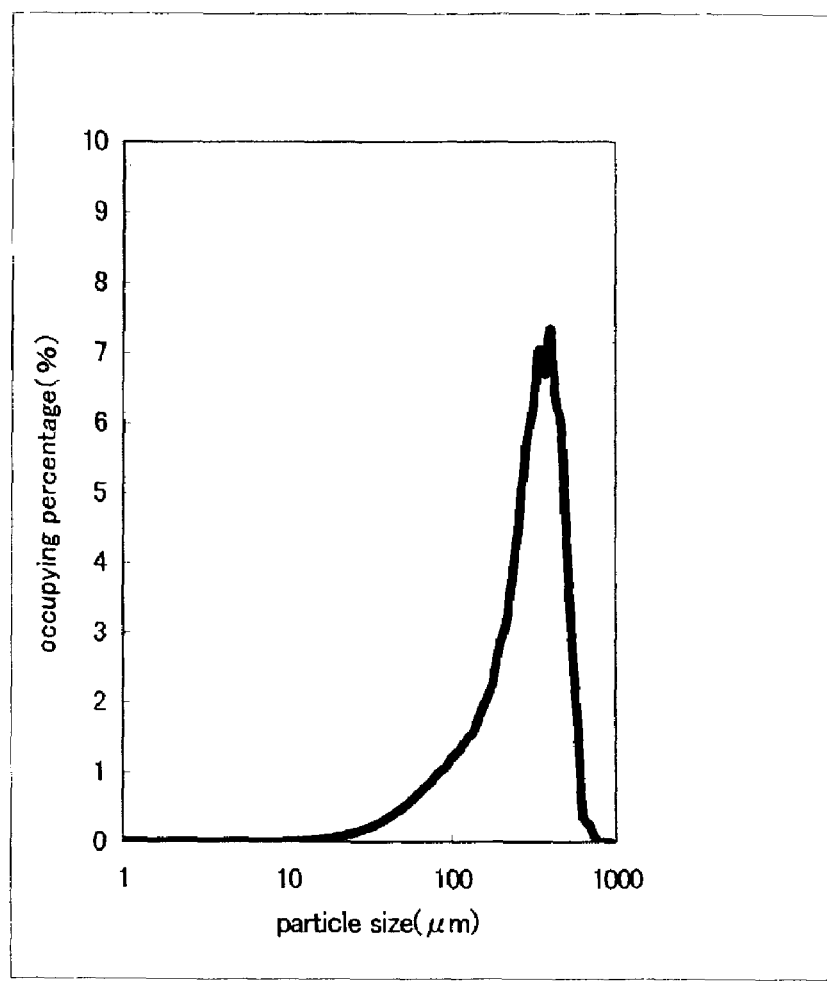
FIG. 1 shows the result of measuring APM particle size distribution for the APM slurry of sample 1 and sample 3 using a Lasentec D600L [FBRM] of an inline type of monitoring system manufactured by Lasentec in which an ordinate shows an occupying percentage (%) while an abscissa shows particle sizes (μm).

The inventors have found that flocculation of an APM slurry is greatly dependent upon the correlation between the APM particle size and the pH of the slurry.

The inventors have further found that when particle size distribution of the APM slurry is measured, which can also measure the aggregated state of APM particles, and the particle size distribution is exhibited as a single peak, the slurry is stable whereas if the particle size distribution exhibits a plurality of peaks, flocculation will occur.

Thus, in one embodiment of the invention, a process for producing a stable APM slurry that is also maintained at a pH for preserving antimicrobial conditions, by formulating the slurry with particles not more than 10 μm in median size and which exhibit a monomodal size distribution, in contrast to a bi-or multi-modal distribution, at not more than 1000 μm.

Thus, with this process it is possible to prepare a slurry of APM that can also be formulated at a pH of not more than 4 to maintain conditions suitable for preservation of the slurry and antimicrobial conditions. In one embodiment, the pH is 2 or 3.

In the APM slurry, one embodiment of the invention is to utilize APM particles that have a median size of not more than about 6 μm. In another embodiment, the APM particles have a median size of not more than about 3 μm.

Therefore, as a result of the method described above, another embodiment of the present invention is a stable APM slurry, which contains APM particles having a median size of not more than 10 μm, formulated at a pH of not more than 4, and where the APM particle size distribution is monomodal, e.g., one peak rather than multiple peaks). In one embodiment, the pH is from 2 or 3. In another embodiment the APM particles have a median size of not more than about 6 μm. In another embodiment, the APM particles have a median size of not more than about 3 μm.

The APM slurry described herein can contain, in addition to the APM and the dispersing medium (such as water), pH adjusting agents, carriers (such as D-sorbitol), bulking agents, excipients and other common ingredients useful for liquid sweeteners. In addition, various preservation agents, such as sodium benzoate, can also be included to provide antimicrobial conditions in the APM slurry. When sodium benzoate is used as the preservation agent, the pH of the APM slurry is not more than about 4.

The concentration of the APM in the slurry can be varied depending on the particular use and/or need of the user. For example, the concentration of APM can be selected to be in an amount of more than its solubility in the edible dispersing medium (such as water) and which is within the preferred pH range. In one embodiment, 3 to 15 g of APM is mixed per 100 g of the edible dispersing medium and, in another embodiment, 5 to 10 g per 100 g of the edible dispersing medium at room temperature.

To prepare the APM slurry it is generally preferred to avoid foaming during the process as such foaming can result in flocculation in the slurry.

The APM particles can be dried and ground using conventional drying methods, for example, a gas stream drier (such as Micron Drier manufactured by Hosokawa Micron K. K.) to adjust to the APM particle size. Other examples of suitable drying methods include air drying, a method using a fluidized drier, a conical drier, and a shelf drier.

Although it is preferable to select the crystallization conditions so that the dried APM particles are within the targeted size and distribution, it is also possible to further adjust the particle size by common grinding methods to achieve the appropriate sized APM particles. To adjust the size and/or size distribution of the APM particles, which are prepared by a one-step or two-step crystallization, the particles (crystals) can be ground using conventional grinding methods, such as a jet mill. In another aspect of the invention, the crystallization of the APM can be controlled such that the appropriate sized APM particles can be directly dried without further grinding. However, in a preferred embodiment, a gas steam drier can be used to dry and/or grind the particles while preventing the formation of undesirable foam and which attains the object APM slurry as when a jet mill is used to adjust the particle size, the efficiency of producing a stable APM slurry that is not subject to flocculation drops.

With respect to using a gas stream drier, the gas steam drier allows for short drying time, which particular advantageous because it minimizes heat damage and allows for continuous processing.

The APM slurry can be used as a liquid sweetener, for example, a table sweetener or may be added to various food and beverages, such as soft drinks during or after the manufacturing process.

Another embodiment of the invention is a method for assessing the stability of an APM slurry by determining the size distribution of the APM particles in the APM slurry, whereby if a single peak or monomodal distribution in the range of not more than about 1000 μM in size is observed (rather than multiple peaks or bi-/multi-modal distribution), the APM slurry is stable for storage. In one embodiment of this method of assessment, the APM particles have a median diameter of not more than 10 μm, in another embodiment, the APM particles have a median diameter of not more than 6 μm, and in another embodiment, a median diameter of not more than 3 μm. In another embodiment of this method for assessing the stability of an APM slurry, the slurry is also formulated at a pH of not more than 4.0 to facilitate the preservation of the slurry and maintain optimum antimicrobial conditions. In alternate embodiments, the pH is can be 2 or 3.

The particle size distribution can be measured with any device that preferably allows the measurement in a non-destructive manner. A preferred device for the measurement is the Lasentec D600L (FBRM), which is an inline type of monitoring system manufactured by Lasentec.

With respect to showing a single peak or exhibiting a monomodal particle size distribution, the phrase refer to where only one peak or a monomodal size distribution is observed (in contrast to bi- or multi-modal distribution peaks) but also where any additional peaks that may be identified would either not be easily recognized or is considered not significant according to normal practices in the art. An example of a single peak or monomodal size distribution is shown in FIG. 1.

To measure the median APM particle diameter various size distribution meters commonly used for measuring particle sizes for powders can be used, for example LA920 (manufactured by Horiba K.K.)

As a result of this method, it is also possible to monitor the size and distribution of APM particles in a manufacturing process so as to confirm the desirable characteristics of the APM to be used in formulating a slurry. For example, using the aforementioned Lasentec D600L (FBRM) the detection of a single peak, such as that shown in FIG. 1 will confirm the presence of the desired APM particles. When a single peak is confirmed in advance, it is not necessary thereafter to repeatedly check the size of particles in the slurry. However, since there is a possibility of slight variations when manufacturing the slurry, which would affect the stability of the resultant slurry, the assessment of the APM particle size is preferably performed for each manufacturing lot in accordance with the methods described in this application.

Having generally described this invention, a further understanding can be obtained by reference to certain specific examples which are provided herein for purposes of illustration only and are not intended to be limiting unless otherwise specified.

EXAMPLES

Preparation of APM of Various Particle Sizes

Example 1

An aqueous starting material solution (380 L; 55° C.; initial concentration of APM: 4.4% by weight) with 17.7 kg of dissolved aspartame (APM) was charged in a crystallization apparatus made of stainless steel having a diameter of 400 mm and equipped with a jacket outside and a cooling plate inside, a cooling medium at 0° C. was circulated in the jacket and the cooling plate, which cooling was carried out for 3 hours. After approximately 1 hour, the whole solution became a pseudo-solid phase. The pseudo-solid phase APM crystals were dropped into a receiving vessel equipped with a cooling coil and a stirrer, disintegrated to slurry and cooled further—cooled from 16° C. to 7° C. in the receiving vessel. The slurry prepared as such was filtered and dehydrated using a centrifugal separator having a diameter of 36 inches whereupon wet APM crystals containing 30% water were obtained. The wet APM crystals obtained by such a static crystallization were continuously supplied to a Micron Drier (manufactured by Hosokawa Micron K. K.) using a screw feeder. They were dried until the water content became 2.6% to give dry APM crystals having an average particle size (median diameter) of about 20 μm.

The above was prepared and adjusted into samples of the following conditions of (a), (b) and (d) and used for the manufacture of APM slurry.

Example 2

Aspartame (APM) hydrochloride crystals (24 kg) were dissolved in 320 L of water and adjusted to pH 2.5 using 1.3 L of 28% aqueous solution of NH$_4$OH together with heating at 36° C. and stirring. After that, it was heated at 65.5° C. and adjusted to pH 4.9 with 3.0 L of 28% aqueous solution of NH$_4$OH. The aqueous solution containing 4.9 g/dl of α-APM was transferred to a cylindrical crystallizing tube of 400 mm inner diameter and 3000 mm of full length equipped with a jacket having no stirring device and then cooling water at −5° C. was flown into the jacket for 3.5 hours. The bottom of the crystallizing tube was opened and the solution was transferred to a crystallizing vessel equipped with a stirrer and continuously cooled with stirring for one night until the temperature became 5° C. The resulting slurry (350 L) was filtered and dehydrated using a centrifugal separator having a diameter of 36 inches to give wet crystals of APM containing 38% of water. These wet APM crystals were continuously supplied to a Micron Drier (manufactured by Hosokawa Micron K. K.) using a screw feeder. That was dried until the water content became 2.7% to give dry crystals of APM having an average particle size (median diameter) of about 6 μm.

The above was prepared and adjusted into the sample of the following condition of (c) and used for the manufacture of APM slurry.

Example 3

Particles were prepared and adjusted as per the following conditions (a) to (d) using the APM prepared in Examples 1 and 2; and used for the manufacture of APM slurry:
 (a) APM of about 3 μm ground for adjusting the particle size (sample 1);
 (b) APM of about 6 μm ground for adjusting the particle size (sample 2);
 (c) APM of about 6 μm where no particle size adjustment was carried out (sample 3); and
 (d) APM of about 20 μm where no particle size adjustment was carried out (sample 4).

The particle size of APM was measured in terms of a median diameter using a particle size distribution meter LA920 (manufactured by Horiba K.K.) equipped with a kit for measuring dry substances, such as powder.

To adjust the particle size, APM was ground using a jet mill (STJ-475 manufactured by Seishin Kigyo K. K.).

Example 4

APM slurries were prepared to the formulations in Table 1 using the samples 1 to 4 described in Example 3.

TABLE 1

APM Slurry (unit: g)

| Ingredients | Compounding Amounts |
| --- | --- |
| ① APM | 16.000 |
| ② D-Sorbitol | 202.400 |
| ③ CMC sodium (*1) | 0.020 |
| ④ Methyl cellulose | 0.100 |
| ⑤ Lecithin (*2) | 0.100 |
| ⑥ NaCl | 0.035 |
| ⑦ 10% HCl | 1.800 |
| ⑧ Deionized water | 28.200 |
| ⑨ Sodium benzoate | 0.400 |
| Total | 249.055 |

(*1) manufactured by Tokyo Kasei Kogyo K. K.
(*2) manufactured by Taiyo Kagaku K. K.

APM and D-sorbitol were stirred and mixed at 300 rpm for 15 minutes to prevent foaming; and then CMC sodium (carboxymethyl cellulose sodium), methyl cellulose, lecithin, NaCl, 10% HCl and deionized water, which were previously mixed and dissolved were added thereto. Sodium benzoate was then added and the mixture was stirred and mixed again at 300 rpm for 15 minutes to yield an APM slurry (samples 1 to 4). The pH value of the resulting slurry was 4.0.

Example 5

The resulting slurry was statically preserved in a 50-ml graduated cylinder for 3 weeks at ambient temperature and the stability of the slurries was assessed and is shown in Table 2.

TABLE 2

Result of Evaluation of Physical Property

| Sample Nos. | After Preserved for 3 Weeks |
| --- | --- |
| 1 | stable |
| 2 | flocculation generated |
| 3 | stable |
| 4 | particles precipitated |

Example 6

Immediately after the slurries of samples 1, 2, and 3 were manufactured, the APM particle size distributions were measured by a Lasentec D600L [FBRM]. The results are shown in FIG. 1 and FIG. 2.

Figure 2:
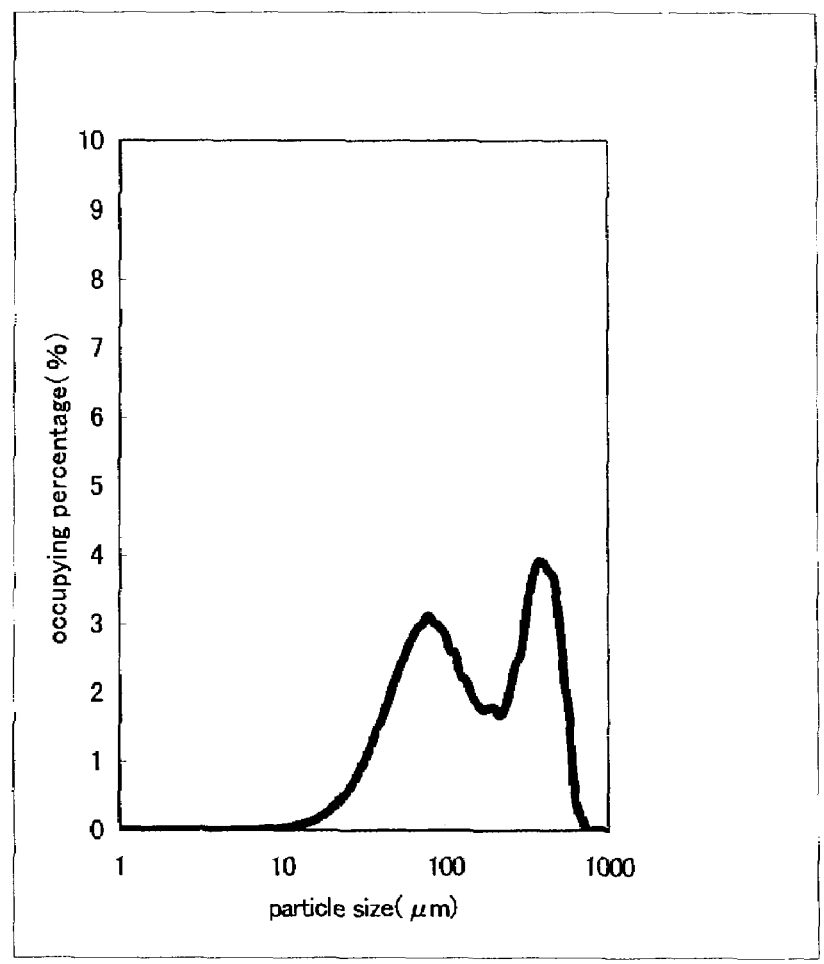
FIG. 2 shows the result of measuring APM particle size distribution for the APM slurry of sample 2 by a Lasentec D600L [FBRM] of an inline type of monitoring system manufactured by Lasentec in which an ordinate shows an occupying percentage (%) while an abscissa shows APM particle size (μm).

The APM slurries of the samples 1 and 3 showed a pattern having a single peak as shown in FIG. 1 while the APM slurry of the sample 2 showed a pattern having a plurality of peaks as shown in FIG. 2.

It is noted from the above that a stable slurry where APM particles are not flocculated in the APM slurry but are homogeneously dispersed shows a pattern of FIG. 1, i.e. a single peak within a range of 1000 μm or less. It is apparent from the above that the APM slurry showing substantially a single peak as in the pattern of FIG. 1 is stable. On the other hand, it was confirmed that the APM slurry showing a plurality of peaks as in FIG. 2 was flocculated during the preservation (storage) and was unstable.

EFFECT OF THE INVENTION

The present invention provides a stable APM slurry where precipitating property and flocculation (physical preservation stability) are improved and microbiological preservation stability is maintained and also provides a method for the judgment thereof. Accordingly, the present invention is very useful in industry particularly in the field of manufacture and utilization of products where a sweetener and APM are present in a form of stable slurry.

In accordance with the present invention, it is possible to provide more stable dispersed product (APM slurry) in a stable manner even after preservation of the product for a long period from its manufacture and it is also possible to previously judge such a dispersed product.

The present application claims priority to Japanese Patent Application No. 2001-358280 filed on Nov. 22, 2001, the contents of which are incorporated herein by reference.

All of the references cited herein, including patents, patent applications, and publications, are hereby incorporated in their entireties by reference.

Obviously, numerous modifications and variations of the present invention are possible in light of the above teachings. It is therefore to be understood that within the scope of the appended claims, the invention may be practiced otherwise than as specifically described herein.

What is claimed is:

1. A process for preparing an aspartame slurry, comprising adjusting the median diameter size of aspartame crystals to not more than 10 μm;
mixing the aspartame crystals in a dispersing medium; and
adjusting the pH of the resultant slurry to a pH suitable for maintaining antimicrobial conditions in the slurry, wherein after the mixing, the slurry exhibits a monomodal size distribution at not more than about 1000 μm.

2. The process of claim 1, wherein the median diameter size of aspartame crystals is not more than 6 μm.

3. The process of claim 1, wherein the median diameter size of asparatame crystals is not more than 3 μm.

4. The process of claim 1, wherein the pH is adjusted to not more than 4.0.

5. The process of claim 1, wherein the pH is adjusted to not more than 3.0.

6. The process of claim 1, wherein the pH is adjusted to not more than 2.0.

7. The process of claim 1, which further comprises mixing sodium benzoate into the dispersing medium.

8. The process of claim 1, wherein the median size of the aspartame crystals are adjusted with a gas steam drier.

9. An aspartame slurry, which comprises aspartame crystals which are of a median particle size of not more than 10 μm, which has a pH suitable for maintaining antimicrobial conditions in the slurry, and wherein the slurry exhibits a monomodal size distribution at not more than about 1000 μm.

10. The aspartame slurry of claim 9, wherein the median diameter size of aspartame crystals is not more than 6 μm.

11. The aspartame slurry of claim 9, wherein the median diameter size of aspartame crystals is not more than 3 μm.

12. The aspartame slurry of claim 9, wherein the pH is not more than 4.0.

13. The aspartame slurry of claim 9, wherein the pH is not more than 3.0.

14. The aspartame slurry of claim 9, wherein the pH is not more than 2.0.

15. The aspartame slurry of claim 9, which further comprises sodium benzoate.

16. A process for assessing the stability of an aspartame slurry, comprising
measuring the median particle size distribution of the aspartame in the slurry, wherein the presence of a monomodal size distribution in a range of not more than 1000 μm is indicative that the aspartame slurry is stable, and wherein the presence of a multimodal size distribution is indicative that the aspartame slurry is not stable.

* * * * *